(12) United States Patent
Lee et al.

(10) Patent No.: US 6,523,420 B2
(45) Date of Patent: Feb. 25, 2003

(54) TENSION MEASUREMENT APPARATUS FOR POGO PIN

(75) Inventors: Ho-Yeol Lee, Yongin-shi (KR);
Doo-Sun Lee, Yongin-shi (KR);
Byoung-Joo Kim, Yongin-shi (KR);
Jung-Ho Kim, Yongin-shi (JP)

(73) Assignee: Samsung Electronics Co., Ltd., Kyungki-do (KR)

( * ) Notice: Subject to any disclaimer, the term of this patent is extended or adjusted under 35 U.S.C. 154(b) by 0 days.

(21) Appl. No.: 09/949,852

(22) Filed: Sep. 12, 2001

(65) Prior Publication Data

US 2002/0148301 A1 Oct. 17, 2002

(30) Foreign Application Priority Data

Apr. 11, 2001 (KR) .............................. 01-19306

(51) Int. Cl.[7] .................................. G01N 3/08
(52) U.S. Cl. ......................................... 73/831
(58) Field of Search .................. 73/818, 827, 831, 73/832, 841, 847, 796

(56) References Cited

U.S. PATENT DOCUMENTS

| | | | |
|---|---|---|---|
| 4,314,203 A | * 2/1982 | Haberlein | 324/238 |
| 5,087,878 A | * 2/1992 | Belmore et al. | 324/72.5 |
| 5,451,883 A | * 9/1995 | Staab | 174/207 |
| 5,818,248 A | * 10/1998 | St. Onge | 324/754 |
| 6,014,904 A | * 1/2000 | Lock | 73/865.5 |
| 6,084,421 A | * 7/2000 | Swart et al. | 324/755 |
| 6,359,456 B1 | * 3/2002 | Hembree et al. | 324/754 |

\* cited by examiner

*Primary Examiner*—Max Noori
(74) *Attorney, Agent, or Firm*—Lee & Sterba, P.C.

(57) ABSTRACT

A tension measurement apparatus for a pogo pin having a height adjusting device for adjusting a height to be measured vertically, on which a device for measuring a tension of the pogo pin is mounted to be vertically movable according to the operation of the height adjusting device. The measurement apparatus preferably includes a vertical moving supporter mounted on the height adjusting device, a fixing member disposed to be coupled with or separated from the vertical moving supporter, a moving rail rotatably connected to the fixing member, a coupler mounted on the moving rail to be movable within the range of a given distance, connected to the tension measurement device. The tension measurement apparatus of the present invention can measure the tension of pogo pins under uniform conditions, while the pogo pins remain in a pogo module, thereby preventing inspection errors due to the pogo pins.

13 Claims, 7 Drawing Sheets

TENSION MEASUREMENT APPARATUS FOR POGO PIN

BACKGROUND OF THE INVENTION

Field of the Invention

The present invention relates to a tension measurement apparatus for testing electrical characteristics of semiconductor devices fabricated on a semiconductor wafer. More particularly, the present invention relates to a tension measurement apparatus for pogo pins in a pogo module arranged to contact a probe card when the electrical characteristics of semiconductor devices fabricated on a semiconductor wafer are tested.

Semiconductor devices such as transistors and integrated circuits are generally fabricated by repeatedly carrying out various processes such as oxidation, photolithography, etching, ion implantation, and the like to a wafer to form a given pattern thereon. However, as the elements incorporated into the semiconductor devices are increasingly integrated, unexpected defects are sometimes made in the semiconductor devices during the fabrication. To inspect the defects, an electrical die sorting (EDS) process is carried out as a post-treatment process.

In the EDS process, the electrical characteristics of semiconductor devices fabricated on the wafer are tested to decide if the devices are normal. A probe apparatus for finding out electrical characteristics of output signals to given input signals is generally used to inspect the devices.

The probe apparatus generally comprises a tester, a tester head, and a probe card which are sequentially disposed above a wafer to be tested. The wafer is held by means of a prober chuck. Between the tester head and the probe card, a pogo module is disposed. The pogo module functions to transmit electrical signals from the tester head to the probe card. For this, the pogo module has several hundred pogo pins disposed in a printed circuit board (PCB).

Each pogo pin comprises a housing disposed in the pogo module to penetrate the pogo module, needles disposed on both ends of the housing, balls disposed between the needles in the housing, and a spring disposed between the balls.

The spring of the pogo pin functions to provide a cushion between the tester head and the probe card when they are connected with each other through the pogo module. However, since the pogo pin is very fragile, it needs to be handled carefully. Also, according to the tension of the spring, the pogo pin may not correctly transmit the electrical signals to the probe card.

To inspect whether a pogo pin is normal, the pogo pin is tested for its external shape and tension. The external shape is generally inspected by eye. However, the tension must be inspected by means of a separate or portable tension measurement device. Conventionally, a portion of pogo pins as samples has been drawn out from the pogo module and then individually tested by means of the separate tension measurement device. Alternatively, a portion of pogo pins has been freely selected among pogo pins mounted in the pogo module and then manually tested by means of the portable tension measurement device.

The method of using the separate tension measurement device has an advantage in that it can correctly measure the tension of the pogo pin, however, it is inconvenient to draw out pogo pins to be used as samples from the pogo module. The convenience of using the portable tension measurement device is advantageous, but it is also problematic in that the force of pushing the pogo pin through the portable tension measurement device is not constant, thereby causing differing measurement results, i.e., the tension measurement can not be carried out under uniform conditions. Consequently, during the tension measurement, devices under test (DUT) can be damaged due to carelessness of an inspector. Also, a pogo pin may be damaged when it is pushed with excessive force by the portable tension measurement device.

SUMMARY OF THE INVENTION

Therefore, it is a feature of an embodiment of the present invention to provide a new tension measurement apparatus for pogo pins in a pogo module used in inspecting semiconductor devices to prevent inspection errors due to the pogo pins, in which the new tension measurement apparatus for pogo pins can correctly measure the tension of the pogo pins without having to remove them from the pogo module.

It is another feature of an embodiment of the present invention to provide a new tension measurement apparatus for pogo pins, which can measure the tension of pogo pins in a probe module under uniform conditions.

It is yet another feature of an embodiment of the present invention to provide a new tension measurement apparatus for pogo pins, which can easily measure the tension of pogo pins regardless of the position of the pogo pins mounted in a pogo module.

These and other features are provided, according to an embodiment of the present invention, by a tension measurement apparatus for pogo pins comprising a means for adjusting vertically a height to be measured, and a means mounted on the height adjusting means for measuring a tension of the pogo pin, wherein the means for measuring a tension of the pogo pin is vertically movable, according to the operation of the height adjusting means.

In a preferred embodiment of the present invention, the tension measurement apparatus further includes means for mounting the tension measuring means on the height adjusting means and moving it in a horizontal direction. The mounting and moving means comprises a vertical moving supporter mounted on the height adjusting means to be vertically movable according to the operation of the height adjusting means, a fixing member disposed to be connected with and separable from the vertical moving supporter, a moving rail rotatably connected to the fixing member, and a coupler for holding the tension measuring means mounted on the moving rail to be movable within the range of a given distance together with the tension measuring means.

The vertical moving supporter of the mounting and moving means may comprise at least one vertical support fixed to the height adjusting means, a horizontal support connected with a bottom surface of the vertical support, and a coupling projection formed on a side of the vertical support. The coupler of the mounting and moving means may comprise a latch plate for hanging and supporting the tension measuring means and a fixing plate for mounting the latch plate movably on the moving rail. Also, the fixing member of the mounting and moving means can comprise a connecting pin having a screw portion and a handle for rotating it, a connecting plate having a screw hole for receiving the screw portion of the connecting pin to be engaged therewith, and a body having a hole for receiving the connecting pin formed on one side thereof, a recess for receiving the connecting plate formed on a lower portion of the hole for receiving the connecting pin, and a penetration hole for receiving the coupling projection formed between the hole for receiving the connecting pin and the recess to fasten the fixing member to the coupling projection by the connecting pin and plate.

The moving rail of the mounting and moving means is rotatably connected to the fixing member through a rotating axis disposed on the other side of the fixing member and corresponding end of the moving rail. The rotating axis may comprise a locking pin having a screw hole formed in the center thereof, bearings for the fixing member and the moving rail inserted in circle shaped grooves formed respectively in the other side of the fixing member and the corresponding end of the moving rail, holes for receiving the locking pin formed respectively in the center of the circle shaped grooves, a ring disposed between the other side of the fixing member and the corresponding end of the moving rail, in which packings are inserted, and a screw for engaging with the screw hole of the locking pin.

Also, the moving rail is rotatable in a horizontal direction within a range of angles from −135 to +135 degrees. The moving rail is connected with an extended moving rail for extending a length of the moving rail in a longitudinal direction. For this, the extended moving rail preferably has the same cross or vertical section as the moving rail.

Also, the height adjusting means of the tension measurement apparatus comprises at least one vertical axis having scales formed in given intervals, a main body disposed to be movable along the vertical axis for measuring a distance moved from a standard position and displaying it, and a base for supporting the vertical axis.

The foregoing and other features and advantages of the present invention will be readily apparent to those of ordinary skill in the art upon review of the detailed description that follows.

BRIEF DESCRIPTION OF THE DRAWINGS

The foregoing and other features and advantages of the present invention will be apparent from the more particular description of preferred embodiments of the present invention, as illustrated in the accompanying drawings in which like reference characters refer to the same parts throughout the different views. The drawings are not necessarily to scale, emphasis instead being placed upon illustrating the principles of the present invention.

DETAILED DESCRIPTION OF THE PREFERRED EMBODIMENTS

Korean Patent Application No. 2001-19306, filed on Apr. 11, 2001, and entitled: "Tension Measuring Apparatus for Pogo Pin," is incorporated by reference herein in its entirety.

The present invention will be described more fully hereinafter with reference to the accompanying drawings, in which a preferred embodiment of the present invention is shown. This invention may, however, be embodied in many different forms and should not be construed as being limited to the embodiment set forth herein; rather, this embodiment is provided so that this disclosure will be thorough and complete, and will fully cover the scope of the invention to those of ordinary skill in the art. Like numbers refer to like elements throughout.

Figure 1:
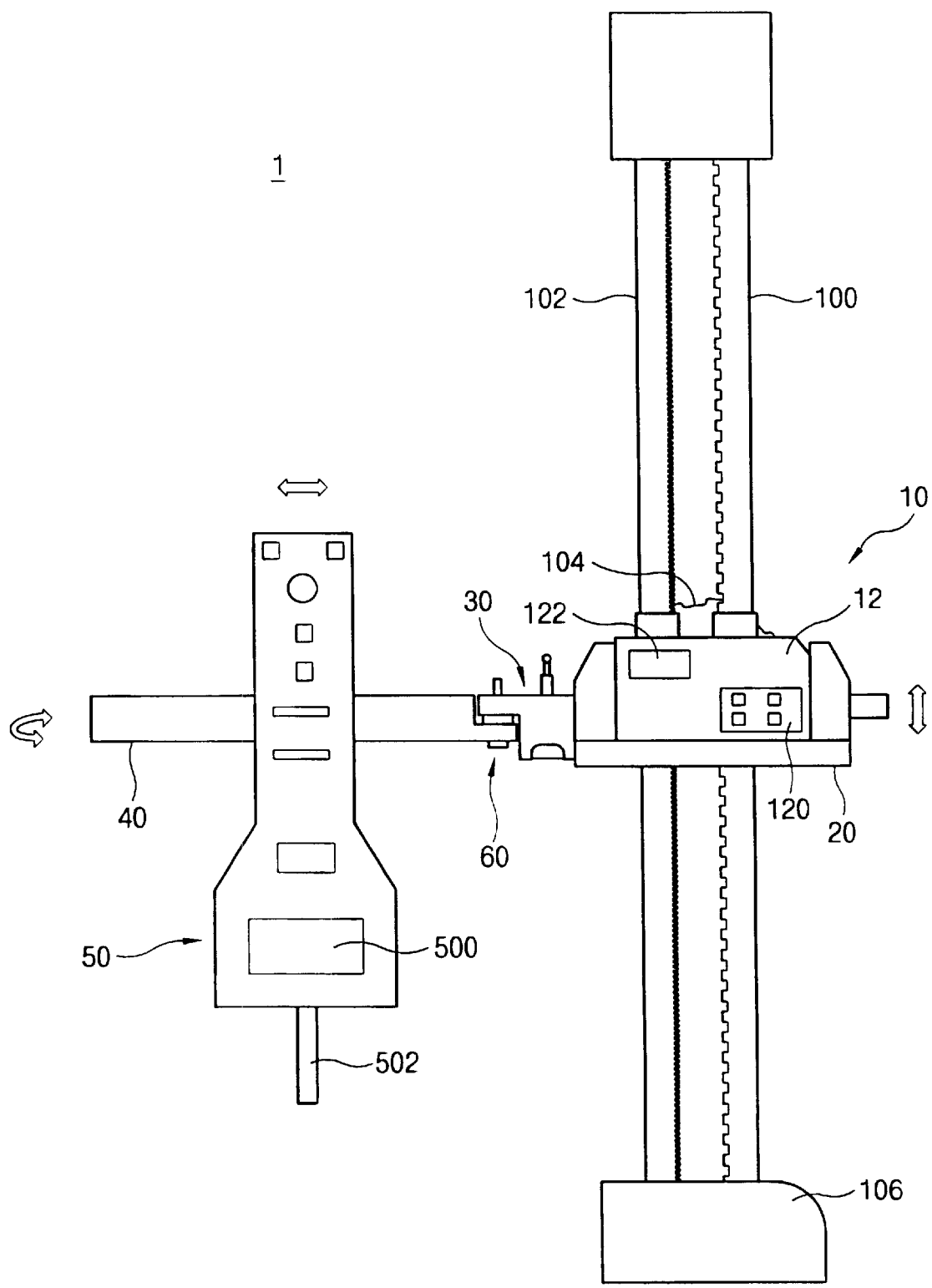
FIG. 1 illustrates an elevational view of a tension measurement apparatus for a pogo pin in accordance with a preferred embodiment of the present invention.

Referring to FIG. 1, there is illustrated an elevational view of a tension measurement apparatus 1 for pogo pins in accordance with a preferred embodiment of the present invention. The tension measurement apparatus 1 of the present invention comprises a height adjusting device 10 for adjusting a height to be measured, a vertical moving supporter 20 mounted on the height adjusting device 10, a fixing member 30 connected to the vertical moving supporter 20, a moving rail 40 connected to the fixing member 30 through a rotating axis 60, a coupler (70 of FIG. 5) mounted on the moving rail 40 to be movable within the range of a given distance, and a tension measuring device 50 mounted on the moving rail 40 through the coupler 70.

The height adjusting device 10 of the tension measurement apparatus 1 includes a main body 12, a first vertical axis 100, a second vertical axis 102, and a base 106. The first and second vertical axes 100, 102 have projected scales of different sizes formed respectively on their inner surfaces opposite to each other. The main body 12 calculates a measuring height through the projected scales. The measuring height, i.e., the height of the main body 12, is adjusted in units of 1/100 to 1 mm. When a width of the height to be adjusted is large, it is adjusted on the base of the first vertical axis 100 having a large projected scale, whereas when the width is small, it is adjusted on the base of the second vertical axis 102 having a small projected scale. The base 106 functions to support the first and second vertical axes 100, 102. Alternatively, the base 106 may include a fixing device for fixing the height adjusting device 10 in a certain place or position. Also, the base 106 may be formed of material which may be easily coupled with the first and second vertical axes 100, 102 when in use and separated therefrom after use, for example, magnetic material in which a state of magnetism is variable according to a setting.

On the front face of the main body 12 is a control panel 120 for setting a standard height, and a display portion 122 for displaying the standard height and any increase or decrease in the measured height from the standard height. Also, on the rear face of the main body 12 is a rotating handle 104 for vertically adjusting the height of the main body 12.

When the height of the main body 12 is vertically adjusted, the vertical moving supporter 20 connected thereto is also moved vertically together with the fixing member 30 and the moving rail 40. Consequently, the tension measuring device 50 mounted on the moving rail 40 is moved vertically. At this time, a measuring tip 502 of the tension measuring device 50 comes to press a pogo pin (82 of FIG. 6) as much as the moved height or distance of the tension measuring device 50, thereby imposing a corresponding load on the pogo pin 82. Accordingly, the tension measuring device 50 measures a tension corresponding to the load imposed on the pogo pin 82, and displays it through a display portion 500. The tension measuring device 50 can use a digital force gauge that can measure the tension within a range of between about 0 to 2,000 g or 0 to 19.60 N (newtons).

The tension measuring device 50 is mounted to be slid onto the moving rail 40 through the coupler 70 as described below. The moving rail 40 is rotatable within a range of angles from −135 to +135 degrees about a rotating axis 60 which will also be described later.

Figure 2:
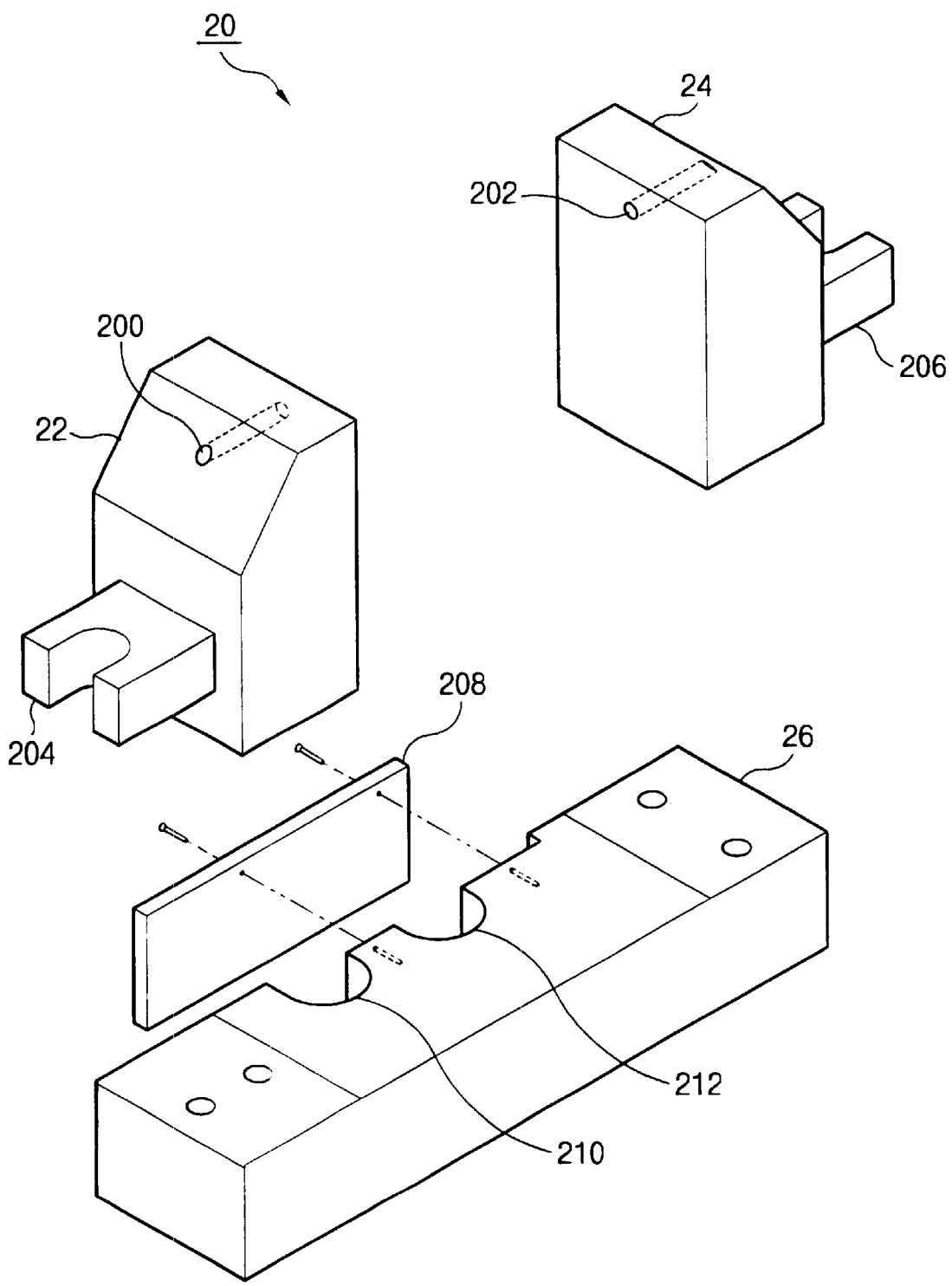
FIG. 2 illustrates an exploded, perspective view of a vertical moving supporter of the tension measurement apparatus shown in FIG. 1.

Referring to FIG. 2, there is illustrated an exploded perspective view of the vertical moving supporter 20 of the tension measurement apparatus 1.

The vertical moving supporter 20 comprises two vertical supports 22, 24 having coupling projections 204, 206 formed respectively on outsides thereof, and a horizontal support 26 connected to lower portions of the vertical supports 22, 24 by means of screws. The coupling projections 204, 206 are formed in a U-shape to be inserted into and fixed on the fixing member 30 as described below. Screw holes 200, 202 are formed on upper portions of the vertical supports 22, 24, for connecting them with the main body 12 of the height adjusting device 10. Also, formed on a side of the horizontal support 26 are grooves 210, 212 for receiving the vertical axes 100, 102 to allow the vertical moving supporter 20 to be vertically movable at a spaced-apart relation to the vertical axes 100, 102. On the grooves 210, 212, a guide plate 208 is fixed by means of screws.

It should be noted that in the specification, the vertical supports 22, 24 are explained as connected to the horizontal support 26 by means of screws, but alternatively, they may be formed in a body.

Figure 3:
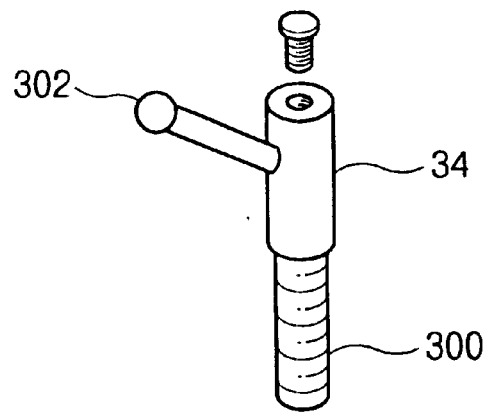
FIG. 3 illustrates an exploded, perspective view of a fixing member of the tension measurement apparatus shown in FIG. 1.
Figure 3:
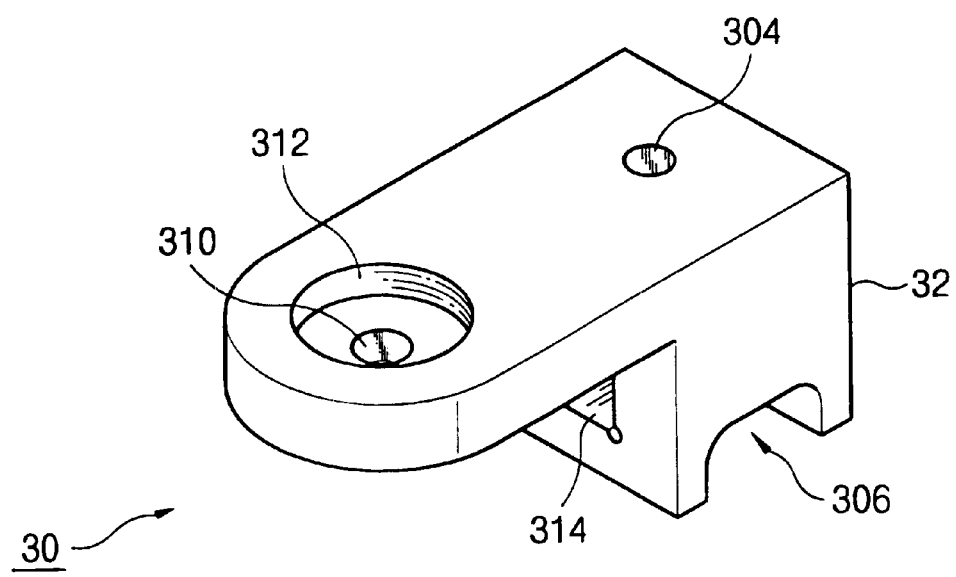
Figure 3:
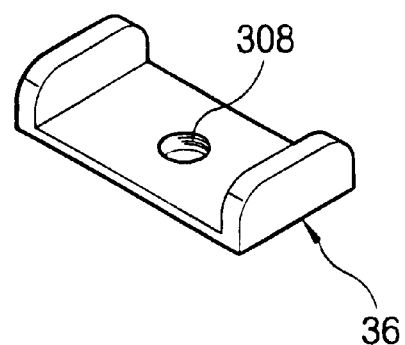

Referring to FIG. 3, there is illustrated an exploded view of the fixing member 30 of the tension measurement apparatus 1. The fixing member 30 comprises a connecting pin 34, a body 32, and a connecting plate 36. The connecting pin 34 has a screw portion 300 and a handle 302 for rotating the connecting pin 34. On one side of the body 32, a hole 304 for receiving the connecting pin 34 is formed. A recess 306 for receiving the connecting plate 36 is formed on a lower portion of the body 32 in which the hole 304 is formed. On the other side of the body 32, a circle shaped groove 312 for receiving a bearing (612 of FIG. 4), which will be explained later, is formed. In the center of the groove 312, a hole 310 for receiving a locking pin (600 of FIG. 4), which will also be explained later, is disposed. Between the hole 304 and the recess 306, a penetration hole 314 for receiving the U-shaped coupling projection 204 is formed. In the center of connecting plate 36 is a screw hole 308 for receiving the screw portion 300 of the connecting pin 34.

Thus, when the coupling projection 204 is inserted into the penetration hole 314, the screw portion 300 of the connection pin 34 is engaged with the screw hole 308 of the connecting plate 36. Consequently, the fixing member 30 is fixed to the coupling projection 204 of the vertical support 22.

Figure 4:
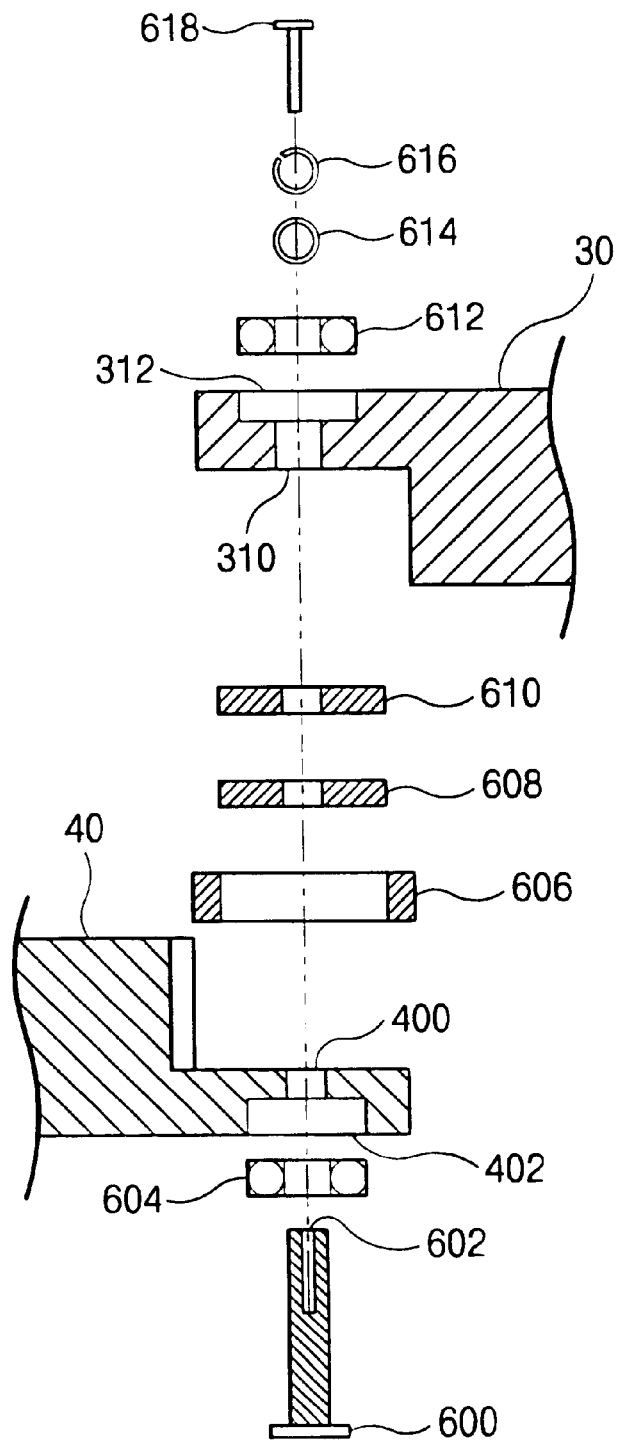
FIG. 4 illustrates an exploded view of a rotating axis for interconnecting the fixing member and a moving rail in the tension measurement apparatus shown in FIG. 1.

Referring to FIG. 4, there is illustrated a rotating axis 60 for interconnecting the fixing member 30 and the moving rail 40. The rotating axis 60 comprises a locking pin 600, a ball bearing 604 for the moving rail 40, an O-shaped ring 606, a ball bearing 612 for the fixing member 30, and a screw 618 for fastening the locking pin 600. A screw hole 602 is formed in the center of the locking pin 600. The bearing 604 for the moving rail 40 is inserted in a circle shaped groove 402 formed in a lower surface of one end of the moving rail 40. A hole 400 for receiving the locking pin 600 is formed in the center of the circle shaped groove 402. The O-shaped ring 606 is disposed between an upper surface of one end of the moving rail 40 and a lower surface of the corresponding end of the fixing member 30. In the O-shaped ring 606, packings 608, 610 are inserted. The bearing 612 for the fixing member 30 is inserted in a circle shaped groove 312 formed in an upper surface of the corresponding end of the fixing member 30. The screw 618 for fastening the locking pin 600 has washers 614, 616.

In the assemblage of the rotating axis 60, first the locking pin 600 is continuously inserted into the bearing 604, the hole 400, the O-shaped ring 606, the hole 310, and the bearing 612. The locking pin 600 is then fastened with the screw 618. As a result, the moving rail 40 is rotatably fixed to the fixing member 30.

It should be noted that the connection structure between the moving rail 40 and the height adjusting device 10 is not intended to be limited to only what is described above, and alternatively, any structure which can transmit the movement of the height adjusting device 10 without shaking and rotating the moving rail 40 in a horizontal direction may be used.

Figure 5:
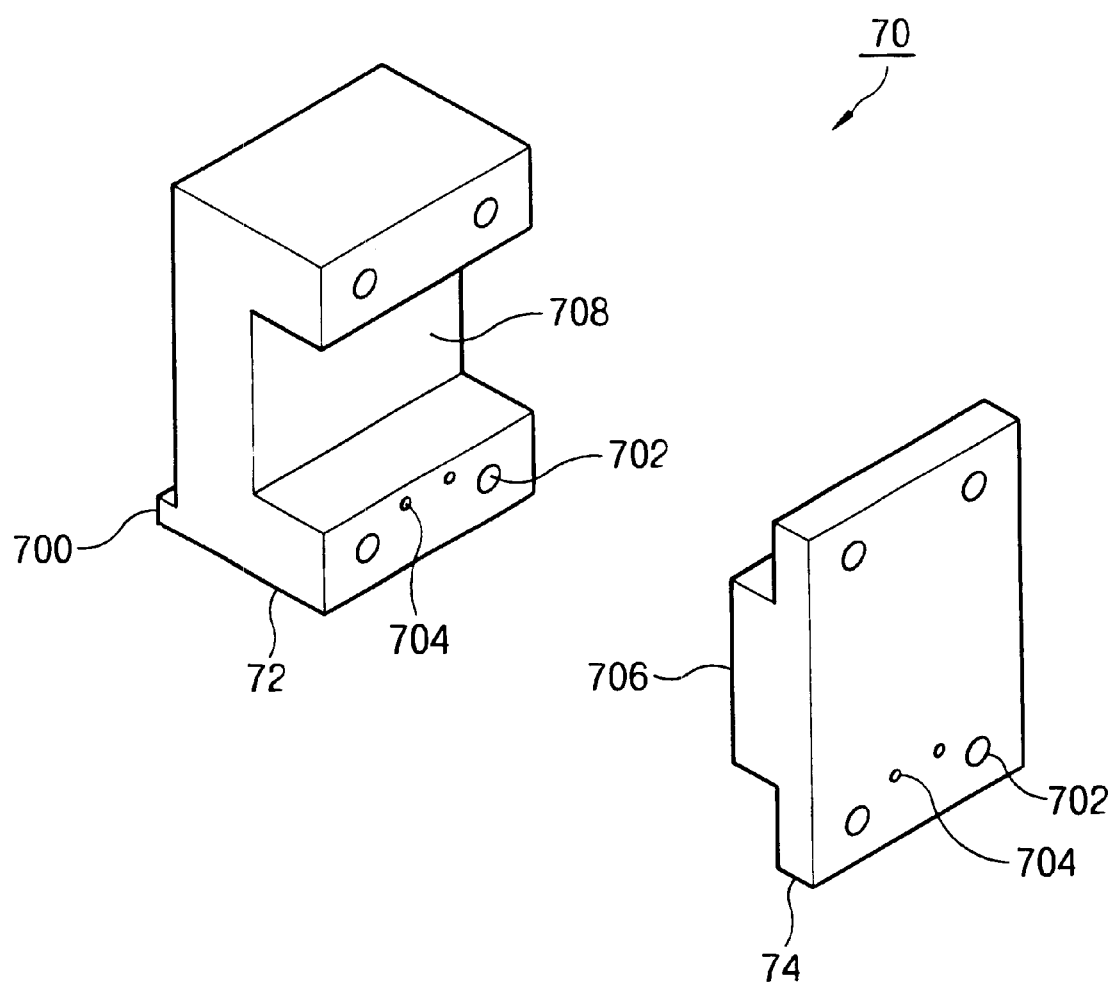
FIG. 5 illustrates an exploded, perspective view of a coupler for mounting a tension measuring device in the tension measurement apparatus shown in FIG. 1.

Referring to FIG. 5, there is illustrated a coupler 70 for mounting the tension measuring device 50 to allow it to be movable onto the moving rail 40. The coupler 70 comprises a latch plate 72 for hanging and supporting the tension measuring device 50 and a fixing plate 74 for mounting the latch plate 72 movably to the moving rail 40. The latch plate 72 has a latch projection 700 for hanging a given portion of the tension measuring device 50 and supporting it, and a recess 708 for receiving the moving rail 40 to allow the latch plate 72 to be movable onto the moving rail 40. The fixing plate 74 includes a supporting projection 706 having a surface for engaging with the moving rail 40 to support it together with the recess 708. The fixing plate 74 is fixed to the latch plate 72 by screws and screw holes 702, 704. Alternatively, rollers or balls may be formed in the recess 708 or the surface of the supporting projection 706 to allow the coupler 70 to move smoothly onto the moving rail 50. Also, the coupler 70 may include a locking portion for locking the coupler 70 in a fixed position.

The operation of the tension measurement apparatus 1 in accordance with the present invention will now be described in detail with reference to FIG. 6.

First, the tension measurement apparatus 1 is assembled in the vicinity of a probe apparatus on which a pogo module 80 is mounted. That is, a vertical moving supporter 20 is mounted on a height adjusting device 10. The fixing member 30 is then fixed to the vertical moving supporter 20. And then, a moving rail 40, a coupler 70 and a tension measuring device 50 are combined in that order.

A plurality of pogo pins 82 are disposed in the pogo module 80 of the probe apparatus. Each pogo pin 82 comprises a housing 820 disposed in the pogo module 80 to penetrate the pogo module 80, needles 822 disposed on both ends of the housing 820, balls 824 disposed in the middle of the housing 820, and a spring 826 disposed between the balls 824.

Next, a tension measuring device 50 is calibrated, i.e., initialized to be adjusted to a zero point. A main body 12 of the height adjusting device 10 is then disposed over a height of the pogo module 80 to allow a measuring tip 502 of the tension measuring device 50 to be positioned above a height of the pogo module 80. Then, the moving rail 40 is rotated about a rotating axis 60 until the tension measuring device 50 is moved over a pogo pin 82 to be measured. After the tension measuring device 50 gains access to the pogo pin 82, the measuring tip 502 of the tension measuring device 50 is aligned with the needle 822 of the pogo pin 82. Next, a handle 104 of the height adjusting device 10 is rotated to be moved down until the measuring tip 502 comes in contact with the needle 822. At this time, the height of the measuring tip 502 as a standard height is set to a zero point. Thereafter, when the handle 104 is again rotated, the measuring tip 502 is moved down to press the needle 822 as much as a given distance d. As a result, a tension of the pogo pin 82 is measured. The measured tension is displayed through a display portion 500 of the tension measuring device 50. The first, or zero, point height and the moved distance d of the measuring tip 502 are used as tension measurement standards when the following pogo pin is measured.

After the tension measurement for the pogo pin 82 is finished, the handle 104 is reversely rotated to move the measuring tip 502 up. Next, the moving rail 40 is again rotated about a rotating axis 60 until the tension measuring device 50 is moved over the following pogo pin to be measured. A tension measurement of the following pogo pin is carried out in the same manner and standard as described above. Thus, the tension measurement of pogo pins is repeated.

The tension standard of the pogo pin is predetermined according to the moved distance d of the measuring tip 502. For example, when the moved distance d of the measuring tip 502 is 3 mm, the tension standard of the pogo pin is 50 gram weight (gw). That is, if the measured tension of the pogo pin is 20 gw, it is too small to be suitable as a tension of the pogo pin. Accordingly, if the spring of the pogo pin is continuously used, a poor contact problem may occur, in which a test head does not come into contact with the probe card. In this case, the pogo pin has to be replaced by a new one. Also, if the measured tension of the pogo pin is 70 gw, the probe card or DUT may be damaged due to the excessive tension of the spring of the pogo pin, and, again the pogo pin has to be replaced by a new one.

Figure 6:
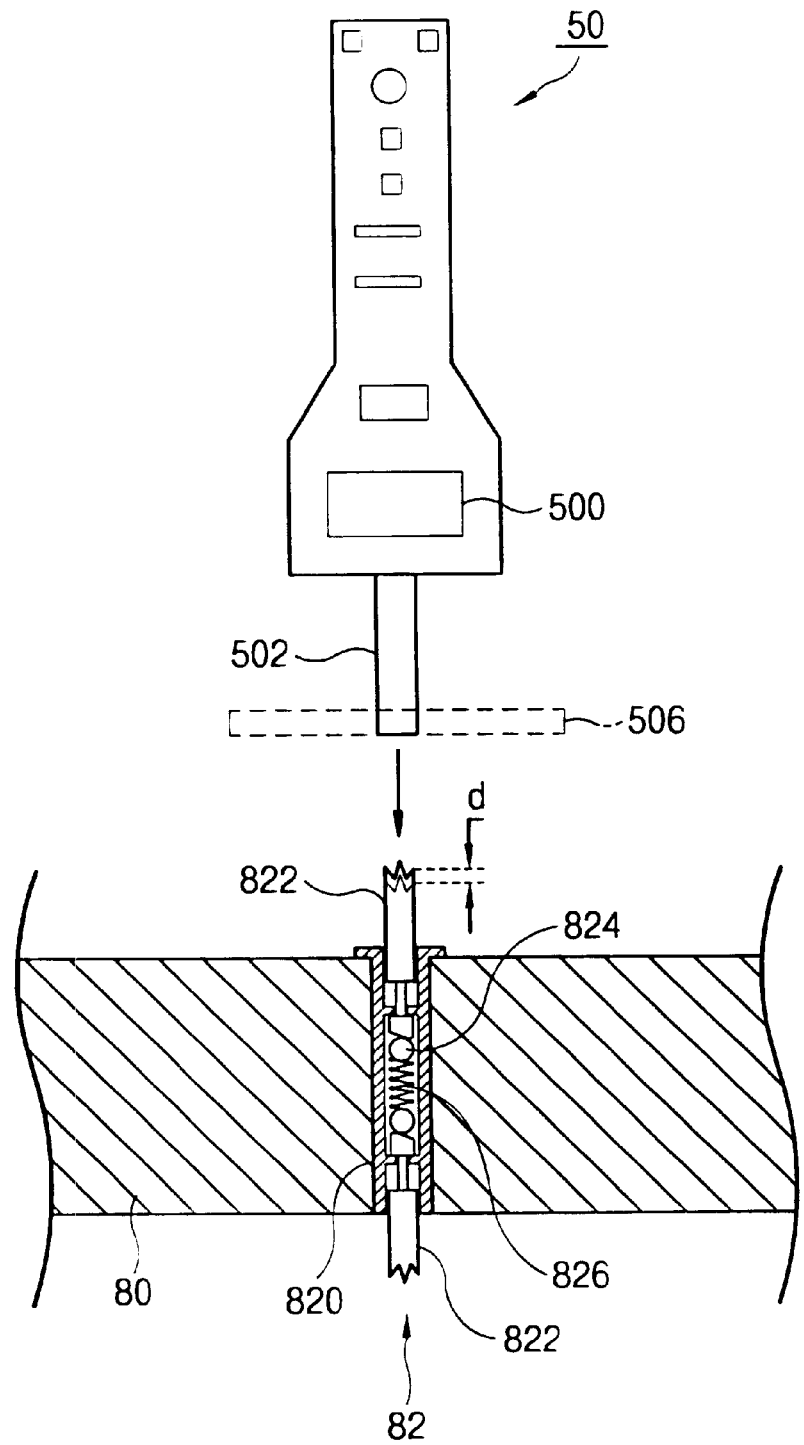
FIG. 6 illustrates a partial, cross-sectional view showing the operation of a tension measuring device of the tension measurement apparatus in accordance with an embodiment of the present invention.

Alternatively, the measuring tip of the tension measuring device 50 can be formed of an enlarged measuring plate 506 to measure a plurality of pogo pins simultaneously, as shown in FIG. 6. At this time, the tension of each of the measured pogo pins is obtained by dividing the overall tension sum by the number of measured pogo pins. The enlarged measuring plate 506 is suitable to inspect whether pogo pins distributed in a wide area are normal, since pogo pins to be used as samples may be tested at the same time.

Figure 7:
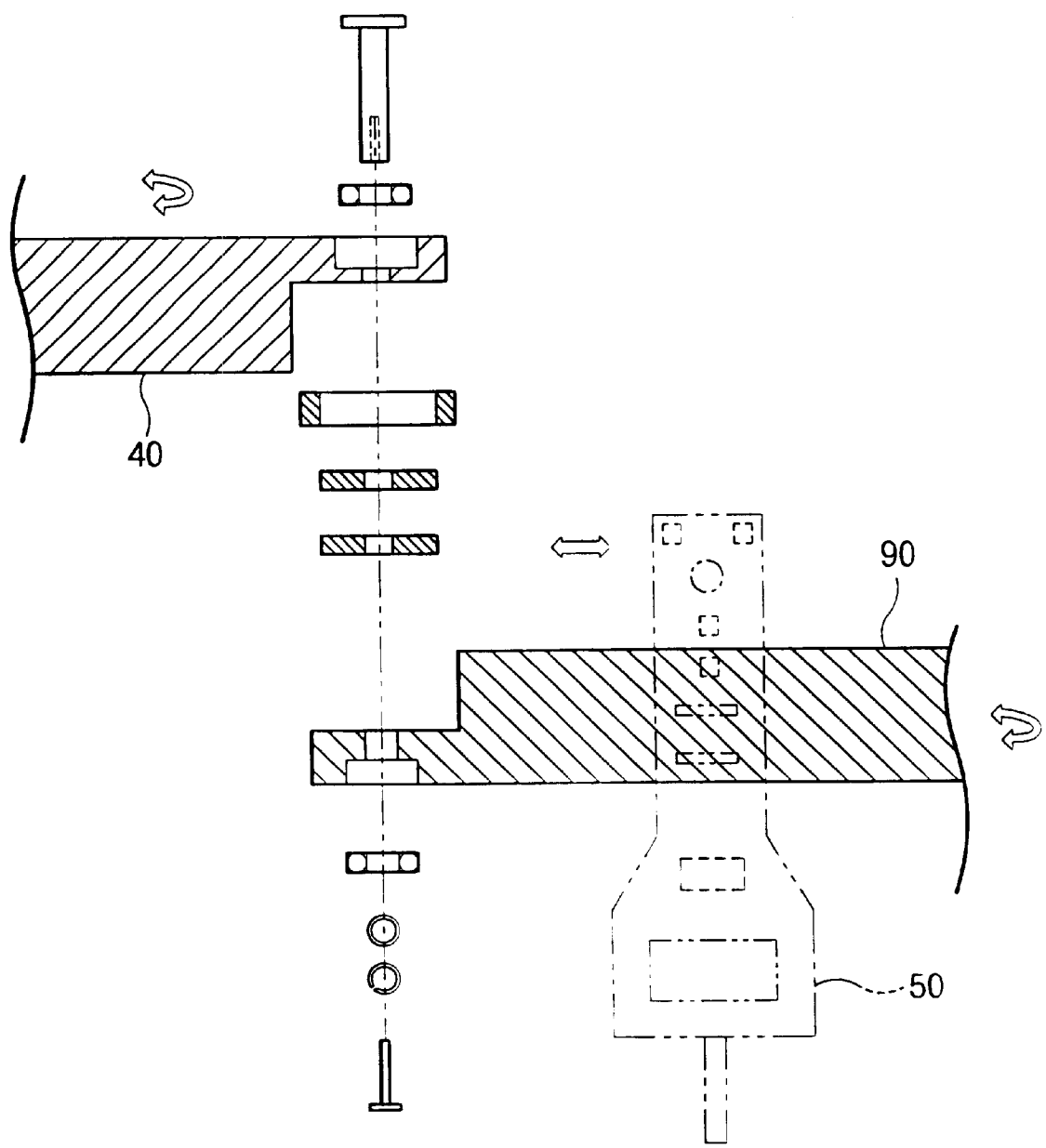
FIG. 7 illustrates a partial, cross-sectional view showing an extended moving rail for extending the length of the moving rail of the tension measurement apparatus shown in FIG. 1.

Referring to FIG. 7, there is illustrated an extended moving rail 90 for extending the length of the moving rail 40 to measure the tension of pogo pins positioned beyond the measurement range of the moving rail 40. The extended moving rail 90 has the same axis structure as the rotating axis 60 for interconnecting the fixing member 30 and the moving rail 40, described above. Also, the extended moving rail 90 is formed to allow the tension measuring device 50 to be freely movable from the moving rail 40. That is, the extended moving rail 90 has the same cross or vertical section as that of the moving rail 40 to allow it to be freely movable through the recess 708 of the latch plate 72. The connecting end of the extended moving rail 90 connected to the moving rail 40 also has the same vertical section as or one smaller than that of the corresponding end of the moving rail 40.

As is apparent from the foregoing description, it may be appreciated that the tension measurement apparatus of the present invention can measure the tension of the pogo pins under predetermined conditions, thereby enhancing the reliability of the measurement results.

Further, the tension measurement apparatus of the present invention can measure the tension of the pogo pins without damage to DUT.

Also, the tension measurement apparatus of the present invention can measure the tension of the pogo pins regardless of the position of the pogo pins mounted in a pogo module.

In the drawings and specification, there has been disclosed a typical preferred embodiment of the present invention and, although specific terms are employed, they are used and are to be interpreted in a generic and descriptive sense only and not for purposes of limitation. Accordingly, it will be understood by those of ordinary skill in the art that various changes in form and details may be made without departing from the spirit and scope of the present invention as set forth in the following claims.

What is claimed is:

1. A tension measurement apparatus for a pogo pin comprising:

height adjusting means for vertically adjusting a height to be measured;

tension measuring means for measuring a tension of the pogo pin, mounted on the height adjusting means to be vertically movable according to the operation of the height adjusting means; and mounting and moving means for mounting the tension measuring means on the height adjusting means and moving the tension measuring means in a horizontal direction, wherein the mounting and moving means includes:

a vertical moving supporter mounted on the height adjusting means to be vertically movable according to the operation of the height adjusting means;

a fixing member disposed to be connected with and separable from the vertical moving supporter;

a moving rail rotatably connected to the fixing member; and a coupler for holding the tension measuring means, mounted on the moving rail to be movable within the range of a given distance together with the tension measuring means.

2. A tension measurement apparatus for a pogo pin as claimed in claim 1, wherein the tension measuring means has a measuring plate which may simultaneously measure a plurality of pogo pins.

3. A tension measurement apparatus for a pogo pin as claimed in claim 1, wherein the tension measuring means is composed of a digital force gauge that can measure the tension within a range of between about 0 to 2,000 g.

4. A tension measurement apparatus for a pogo pin as claimed in claim 1, wherein the vertical moving supporter comprises:

at least one vertical support fixed to the height adjusting means;

a horizontal support connected with a bottom surface of the vertical support; and a coupling projection formed on a side of the vertical support.

5. A tension measurement apparatus for a pogo pin as claimed in claim 1, wherein the coupler comprises:

a latch plate for hanging and supporting the tension measuring means; and a fixing plate for mounting the latch plate movably on the moving rail.

6. A tension measurement apparatus for a pogo pin as claimed in claim 1, wherein the fixing member comprises:
- a connecting pin having a screw portion and a handle for rotating the connecting pin;
- a connecting plate having a screw hole for receiving the screw portion of the connecting pin to be engaged therewith; and
- a body having a hole for receiving the connecting pin formed on a first side thereof, a recess for receiving the connecting plate formed on a lower portion of the body adjacent the hole for receiving the connecting pin, and a penetration hole for receiving the coupling projection formed between the hole for receiving the connecting pin and the recess so as to fasten the fixing member to the coupling projection by the connecting pin and plate.

7. A tension measurement apparatus for a pogo pin as claimed in claim 1, wherein the moving rail is rotatably connected to the fixing member through a rotating axis disposed on a second side of the fixing member, and a corresponding end of the moving rail, wherein the rotating axis comprises:
- a locking pin having a screw hole formed in the center thereof;
- bearings for the fixing member and the moving rail inserted in circle shaped grooves formed respectively in the second side of the fixing member, and the corresponding end of the moving rail;
- holes for receiving the locking pin formed respectively in the center of the circle shaped grooves;
- a ring, having packings inserted therein, disposed between the second side of the fixing member, and the corresponding end of the moving rail; and
- a screw for engaging with the screw hole of the locking pin.

8. A tension measurement apparatus for a pogo pin as claimed in claim 7, wherein the moving rail is rotatable in a horizontal direction within a range of angles from −135 to +135 degrees.

9. A tension measurement apparatus for a pogo pin as claimed in claim 1, wherein the moving rail is connected with an extended moving rail for extending a length of the moving rail in a longitudinal direction.

10. A tension measurement apparatus for a pogo pin as claimed in claim 9, wherein the extended moving rail has the same vertical section as the moving rail.

11. A tension measurement apparatus for a pogo pin as claimed in claim 1, wherein the height adjusting means comprises:
- at least one vertical axis having scales formed in given intervals;
- a main body, disposed to be movable along the vertical axis, for measuring a distance moved from a standard position and displaying the measured distance; and
- a base for supporting the vertical axis.

12. A tension measurement apparatus for a pogo pin as claimed in claim 1, wherein the height of the height adjusting means is adjusted in units of $1/100$ to 1 mm.

13. A tension measurement apparatus for a pogo pin as claimed in claim 11, wherein the base is formed of magnetic material in which a state of magnetism is variable according to a setting.

* * * * *